United States Patent
Nakamura

(10) Patent No.: US 10,860,894 B2
(45) Date of Patent: Dec. 8, 2020

(54) LEARNING DATA GENERATION SUPPORT APPARATUS, OPERATION METHOD OF LEARNING DATA GENERATION SUPPORT APPARATUS, AND LEARNING DATA GENERATION SUPPORT PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

(21) Appl. No.: 16/011,157

(22) Filed: Jun. 18, 2018

(65) Prior Publication Data

US 2019/0005354 A1 Jan. 3, 2019

(30) Foreign Application Priority Data

Jun. 30, 2017 (JP) ................. 2017-129453

(51) Int. Cl.
| | | |
|---|---|---|
| *G16H 30/40* | (2018.01) | |
| *G06K 9/62* | (2006.01) | |
| *G06T 7/00* | (2017.01) | |
| *G16H 30/20* | (2018.01) | |
| *G06N 20/00* | (2019.01) | |

(Continued)

(52) U.S. Cl.
CPC ......... *G06K 9/6262* (2013.01); *G06K 9/6202* (2013.01); *G06K 9/6255* (2013.01); *G06K 9/6256* (2013.01); *G06N 20/00* (2019.01); *G06T 7/0014* (2013.01); *G16H 30/20* (2018.01); *G16H 30/40* (2018.01); *G16H 50/70* (2018.01); *G06N 3/0454* (2013.01); *G06N 3/08* (2013.01); *G06T 2207/10072* (2013.01); *G06T 2207/10132* (2013.01); *G06T 2207/20081* (2013.01); *G06T 2207/20084* (2013.01); *G06T 2207/30096* (2013.01)

(58) Field of Classification Search
CPC .................................................... G16H 30/40
See application file for complete search history.

(56) References Cited

U.S. PATENT DOCUMENTS

| | | | | |
|---|---|---|---|---|
| 8,483,450 B1 * | 7/2013 | Derakhshani | ...... | G06K 9/00597 382/117 |
| 9,846,937 B1 * | 12/2017 | Sharma | ................... | G06T 5/002 |

(Continued)

FOREIGN PATENT DOCUMENTS

| | | |
|---|---|---|
| JP | 2009-219655 A | 10/2009 |
| JP | 4493679 B2 | 6/2010 |
| JP | 2011-67253 A | 4/2011 |

*Primary Examiner* — King Y Poon
*Assistant Examiner* — Michael Burleson
(74) *Attorney, Agent, or Firm* — Birch, Stewart, Kolasch & Birch, LLP

(57) ABSTRACT

Any one of acquired images is set as a reference image, and an image other than the reference image is set as a comparison image. According to a portion or a disease, a first image processing of extracting an anatomic region is executed with respect to the reference image, and a second image processing of extracting an anatomic region is executed with respect to the comparison image. Whether the comparison image is available as correct answer data is determined using the anatomic region of the reference image and the anatomic region of the comparison image. The comparison image determined to be available as the correct answer data is registered as the correct answer data.

12 Claims, 6 Drawing Sheets

(51) Int. Cl.
*G16H 50/70* (2018.01)
*G06N 3/04* (2006.01)
*G06N 3/08* (2006.01)

(56) References Cited

U.S. PATENT DOCUMENTS

| | | | |
|---|---|---|---|
| 2006/0280347 A1* | 12/2006 | Shirahata | A61B 6/00 |
| | | | 382/128 |
| 2008/0247619 A1 | 10/2008 | Li | |
| 2009/0232378 A1 | 9/2009 | Nakamura | |
| 2011/0069873 A1 | 3/2011 | Azemoto et al. | |
| 2011/0085716 A1* | 4/2011 | Chefd'hotel | G06K 9/6215 |
| | | | 382/128 |
| 2015/0066820 A1* | 3/2015 | Kapur | G06N 5/04 |
| | | | 706/12 |

\* cited by examiner

FIG. 6

LEARNING DATA GENERATION SUPPORT APPARATUS, OPERATION METHOD OF LEARNING DATA GENERATION SUPPORT APPARATUS, AND LEARNING DATA GENERATION SUPPORT PROGRAM

CROSS-REFERENCE TO RELATED APPLICATION

This application claims priority from Japanese Patent Application No. 2017-129453, filed on Jun. 30, 2017, the disclosure of which is incorporated by reference herein in its entirety.

BACKGROUND

Field of the Invention

The present invention relates to a learning data generation support apparatus, an operation method of a learning data generation support apparatus, and a learning data generation support program that perform support for generating learning data used in machine learning.

Related Art

In the related art, machine learning has been used for learning features of data to perform recognition or classification of images or the like. In recent years, various learning methods have been developed. Further, as a processing capability of a computer has been enhanced, a processing time has been reduced. Furthermore, a system has been able to perform deep learning for learning features of image data or the like at a deeper level. By performing the deep learning, it is possible to recognize features of images or the like with extremely high accuracy, and thus, it is expected that discrimination performance is enhanced. A large amount of various data is necessary for the deep learning, and data for discrimination of a large number of images is acquired through the Internet or the like.

On the other hand, in accordance with the spread of a medical information system, for the purpose of cooperation of disease diagnosis and sharing of medical information in districts, realization of a wide range electronic medical record system in which data exchange is possible between medical organizations has been performed. As an elemental technology of a wide range electronic medical record system, there is a medical image management system (PACS: picture archiving and communication system) provided in each medical organization. The PACS performs storage, browsing, and management of image data received from an imaging apparatus (modality) such as a computed radiography (CR) apparatus, a computed tomography (CT) apparatus, a magnetic resonance imaging (MRI) apparatus, and a positron emission tomography (PET) apparatus. Further, by managing image data using the digital imaging and communication in medicine (DICOM) standard, it is possible to unitarily manage various kinds of image data.

Further, there is a case where diagnosis using images captured by a plurality of modalities is effective for diagnosis of one disease, and there is a case where two or more kinds of images are compared and interpreted for diagnosis. In the medical image management system, images obtained by imaging the same portion of the same patient using different modalities are accumulated for performing comparison and interpretation. In order to perform accurate comparison and interpretation, it is necessary to find corresponding positions. Methods for registering images and tomographic images captured using two different modalities are disclosed in JP2011-67253A and JP2009-219655A.

In the medical field, similarly, it is desirable to recognize features of images or the like with high accuracy using deep learning or the like. For the deep learning, learning based on a large amount of high-quality data is essential as necessary. In the medical field, it may be considered that data necessary for learning is buried in a large amount of data stored in a medical image management system, and thus, a method for acquiring data to be used in deep learning from image data stored in a medical information system has been reviewed. However, it is not rational to manually discriminate correct answer data from the large amount of data. In recent years, in medical image processing, its performance has been remarkably enhanced, and it has been possible to obtain an accurate result according to the kind of a captured image. Finding of correct answer data from accumulated images obtained by imaging the same subject using the above-mentioned image processing has been reviewed.

SUMMARY

Accordingly, in order to solve the above-described problems, an object of the invention is to provide a learning data generation support apparatus, an operation method of a learning data generation support apparatus, and a learning data generation support program for automatically generating a large amount of various image data necessary for deep learning in a medical field.

According to an aspect of the invention, there is provided a learning data generation support apparatus comprising: acquisition means for acquiring two or more different images obtained by imaging the same portion of a subject; setting means for setting any one of the acquired images as a reference image and setting an image other than the reference image among the acquired images as a comparison image, according to the portion or a disease; image processing means for executing a first image processing of extracting an anatomic region with respect to the reference image according to the portion or the disease, and executing a second image processing of extracting an anatomic region with respect to the comparison image according to the portion or the disease; determination means for determining whether the comparison image is available as correct answer data using the anatomic region of the reference image in the first image processing and the anatomic region of the comparison image in the second image processing; and registration means for registering the comparison image determined to be available as the correct answer data as the correct answer data.

According to another aspect of the invention, there is provided an operation method of a learning data generation support apparatus that includes acquisition means, setting means, an image processing means, determination means, and registration means, comprising: acquiring two or more different images obtained by imaging the same portion of a subject, using the acquisition means; setting any one of the acquired images as a reference image, and setting an image other than the reference image among the acquired images as a comparison image, according to the portion or a disease, using the setting means; executing a first image processing of extracting an anatomic region with respect to the reference image according to the portion or the disease, and executing a second image processing of extracting an anatomic region with respect to the comparison image according to the portion or the disease, using the image processing means; determining whether the comparison image is available as correct answer data using the anatomic region of the reference image in the first image processing and the anatomic region of the comparison image in the second image processing, using the determination means; and registering the comparison image determined to be available as the correct answer data as the correct answer data, using the registration means.

Further, according to still another aspect of the invention, there is provided a learning data generation support program that causes a computer to function as: acquisition means for acquiring two or more different images obtained by imaging the same portion of a subject; setting means for setting any one of the acquired images as a reference image and setting an image other than the reference image among the acquired images as a comparison image, according to the portion or a disease; image processing means for executing a first image processing of extracting an anatomic region with respect to the reference image according to the portion or the disease, and executing a second image processing of extracting an anatomic region with respect to the comparison image according to the portion or the disease; determination means for determining whether the comparison image is available as correct answer data using the anatomic region of the reference image in the first image processing and the anatomic region of the comparison image in the second image processing; and registration means for registering the comparison image determined to be available as the correct answer data as the correct answer data.

The "anatomic region" refers to a region indicating a part or the entirety of an anatomic structure such as an organ or a tissue of the body, which is a region having a specific shape and a specific size that appear on an image. The anatomic region is a region for which a boundary with a peripheral region is detectable, or is a region having light and shade or a texture different from that of the peripheral region. For example, the anatomic region may be a region of an organ, a region of a tissue, or a lesion region.

The first image processing and the second image processing may correspond to at least one of an organ extraction process or a lesion detection process.

The registration means may register the comparison image and the anatomic region obtained from the comparison image as the correct answer data.

The kind of the first image processing may be different from the kind of the second image processing.

The two or more different images may be images captured using two or more different kinds of imaging apparatuses.

The two or more different kinds of imaging apparatuses may be two or more kinds of imaging apparatuses among an MRI apparatus, a CT apparatus, a CR apparatus, a PET apparatus, and an ultrasonic imaging apparatus.

The two or more different images may be images captured at different imaging protocols using the same kind of imaging apparatus.

The same kind of imaging apparatus may be an MRI apparatus, and the different imaging protocols may be a T1 imaging protocol and a T2 imaging protocol.

The two or more different images may be images captured at different time points using the same kind of imaging apparatus.

The learning data generation support apparatus may further comprise analysis means for analyzing a character string in an interpretation report of each of the two or more images, in which the setting means may determine the reference image and the comparison image according to the portion or the disease obtained by the analysis means.

Further, the learning data generation support apparatus may further comprise notification means for notifying that the comparison image is not available in a case where the determination means determines that the comparison image is not available as the correct answer data.

Furthermore, the learning data generation support apparatus may further comprise: modification image display means for displaying the anatomic region of the comparison image for which it is notified that the comparison image is not available in a recognizable manner; modification input reception means for receiving an input for modifying the anatomic region of the comparison image; and modification registration means for registering the anatomic region of the comparison image modified according to the input received by the modification input reception means and the comparison image as the correct answer data.

According to the invention, by setting any one of acquired images as a reference image and setting the other image as a comparison image, according to a portion or a disease, extracting an anatomic region of the reference image and an anatomic region of the comparison image, determining whether the comparison image is available as correct answer data on the basis of the extracted anatomic regions of the reference image and the comparison image, and registering, in a case where it is determined that the comparison image is available, the comparison image as the correct answer data, it is possible to automatically acquire a large amount of various correct answer data necessary for deep learning.

BRIEF DESCRIPTION OF THE DRAWINGS

FIG. 6 is a display example of a comparison image determined to be unavailable.

DETAILED DESCRIPTION

Figure 1:
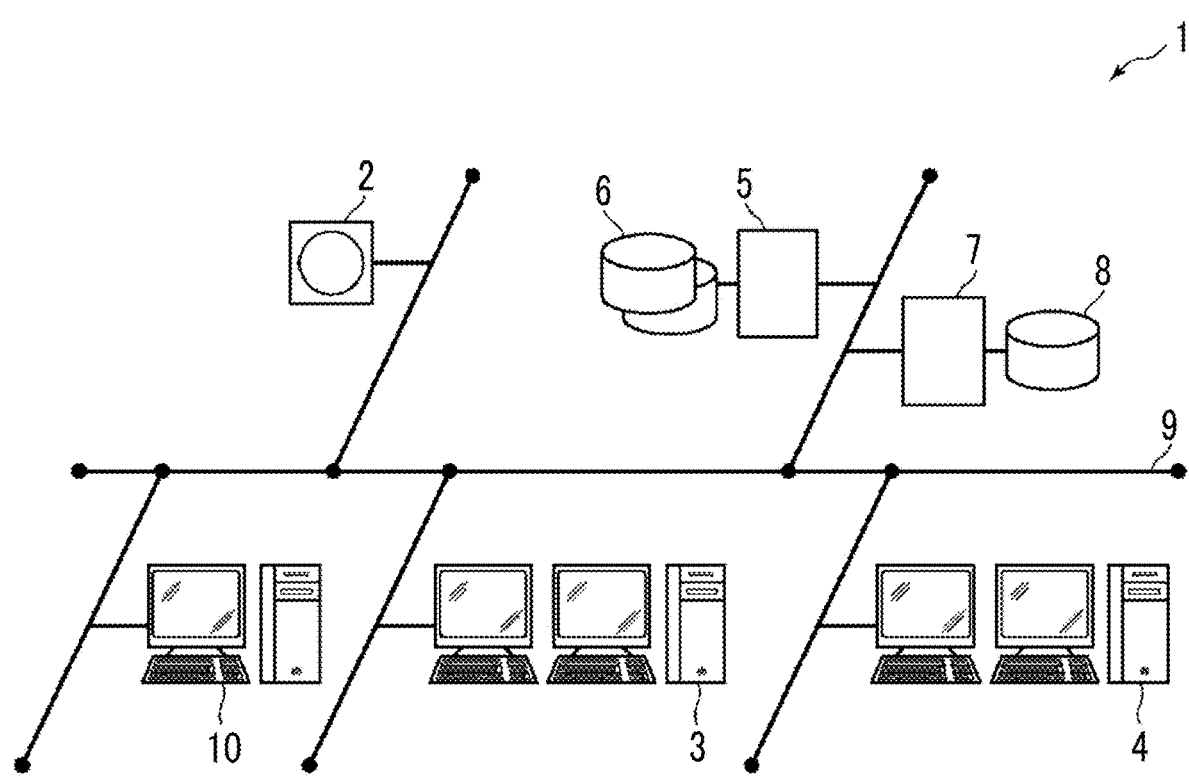
FIG. 1 is a diagram showing a schematic configuration of a medical information system.

FIG. 1 shows a schematic configuration of a medical information system 1 in which a learning data generation support apparatus according to a first embodiment of the invention is introduced. The medical information system 1 is a system for performing imaging and storage of an inspection target portion of a subject, interpretation of a captured image and creation of an interpretation report from a radiologist in a radiology department, and browsing of the interpretation report and detailed observation of an image that is an interpretation target from a doctor in a diagnosis and treatment department that is a client, on the basis of an inspection order given from the doctor in the diagnosis and treatment department using a known ordering system. As shown in FIG. 1, the medical information system 1 is configured so that a modality (an imaging apparatus) 2, a radiologist workstation 3, a diagnosis and treatment department workstation 4, an image management server 5, an image database 6, an interpretation report server 7, and an interpretation report database 8 are connected to each other in a communicable state through a network 9. In each device, an application program for causing the device to function as a component of the medical information system 1 is installed. Further, the application program may be installed from a recording medium such as a CD-ROM, or may be installed after being downloaded from a storage of a server connected through a network such as the Internet.

The modality 2 includes a device that images an inspection target portion of a subject to generate an inspection image that represents the inspection target portion, and adds accessory information (hereinafter, referred to as a DICOM tag) regulated in the DICOM standard to the inspection image for output. As a specific example, a CT apparatus, an MRI apparatus, a positron emission tomography (PET) apparatus, an ultrasonic imaging apparatus, or a CR apparatus that uses a flat panel detector (FPD), or the like may be used.

The radiologist workstation 3 is a computer that is used by a radiologist for interpretation of an image or creation of an interpretation report in a radiology department, and includes a known hardware configuration such as a central processing unit (CPU), a main storage, an auxiliary storage, an input/output interface, a communication interface, an input device, a display device, a data bus, and the like. Further, in the radiologist workstation 3, a known operation system or the like is installed. As the display device, one or plural high definition displays are provided. In the radiologist workstation 3, respective processes such as transmission request of an image with respect to the image management server 5, display of an image received from the image management server 5, automatic detection and highlighting of a lesion likeliness portion in an image, and creation and display of an interpretation report, and the like are performed by executing a software program for the respective processes. Further, the radiologist workstation 3 transmits a generated interpretation report to the interpretation report server 7 through the network 9, and requests registration of the interpretation report into the interpretation report database 8.

The diagnosis and treatment department workstation 4 is a computer that is used by a doctor in a diagnosis and treatment department for detailed observation of an image, browsing of an interpretation report, browsing and input of an electronic medical record, and the like, and includes a known hardware configuration such as a CPU, a main storage, an auxiliary storage, an input/output interface, a communication interface, an input device, a display device, a data bus, and the like. Further, in the diagnosis and treatment department workstation 4, a known operation system or the like is installed. As the display device, one or plural high definition displays are provided. In the diagnosis and treatment department workstation 4, respective processes such as browsing request of an image with respect to the image management server 5, display of an image received from the image management server 5, automatic detection and highlighting of a lesion likeliness portion in an image, browsing request of an interpretation report with respect to the interpretation report server 7, display of an interpretation report received from the interpretation report server 7, and the like are performed by executing a software program for the respective processes. Further, the diagnosis and treatment department workstation 4 transmits a motion picture in endoscopy or the like performed in each diagnosis and treatment department to the image management server 5 through the network 9, and requests registration of the motion picture into the image database 6.

The image management server 5 has a configuration in which a software program that provides a function of a database management system (DBMS) is installed in a general-purpose computer. The image management server 5 is provided with a large capacity storage that configures the image database 6. The storage may be a large capacity hard disk drive connected to the image management server 5 through a data bus, or may be a disk device connected to a network attached storage (NAS) or a storage area network (SAN) connected to the network 9.

In the image database 6, inspection images obtained by imaging a plurality of patients using the modality 2 and accessory information are registered. The accessory information includes information such as an image identification (ID) for identifying each image, a patient ID for identifying a subject, an inspection ID for identifying inspection, a unique identification (UID) allocated to each inspection image, an inspection date on which an inspection image is generated, an inspection time point, the type of a modality used in inspection for acquiring the inspection image, patient information such as a name, an age, and a gender of a patient, an inspection portion (imaging portion), an imaging condition (the presence or absence of usage of a contrast medium, a radiation dose, or the like), and serial numbers or the like in acquiring a plurality of tomographic images in one inspection.

Further, in a case where a browsing request is received from the radiologist workstation 3 through the network 9, the image management server 5 retrieves an inspection image registered in the above-described image database 6, and transmits the extracted inspection image to the radiologist workstation 3 that is a request source.

The interpretation report server 7 has a configuration in which a software program that provides a function of a database management system (DBMS) is installed in a general-purpose computer. In a case where a registration request of an interpretation report is received from the radiologist workstation 3, the interpretation report server 7 registers the interpretation report into the interpretation report database 8 in accordance with a database format.

In the interpretation report database 8, an interpretation report in which information such as an image ID for identifying an interpretation target image or a representative image, a radiologist ID for identifying an image diagnosis doctor who performs interpretation, a lesion name, lesion position information, a doctor's opinion and the degree of conviction of the doctor's opinion is recorded is registered. Further, in the interpretation report, a determination result obtained through a biopsy is recorded.

The network 9 is a local area network through which various devices in a hospital are connected to each other. In a case where the radiologist workstation 3 is provided in another hospital or clinic, the network 9 may be configured to connect local area networks in respective hospitals through the Internet or an exclusive line. In any case, it is preferable that the network 9 has a configuration capable of realizing high-speed transmission of an inspection image, such as an optical network or the like.

Figure 2:
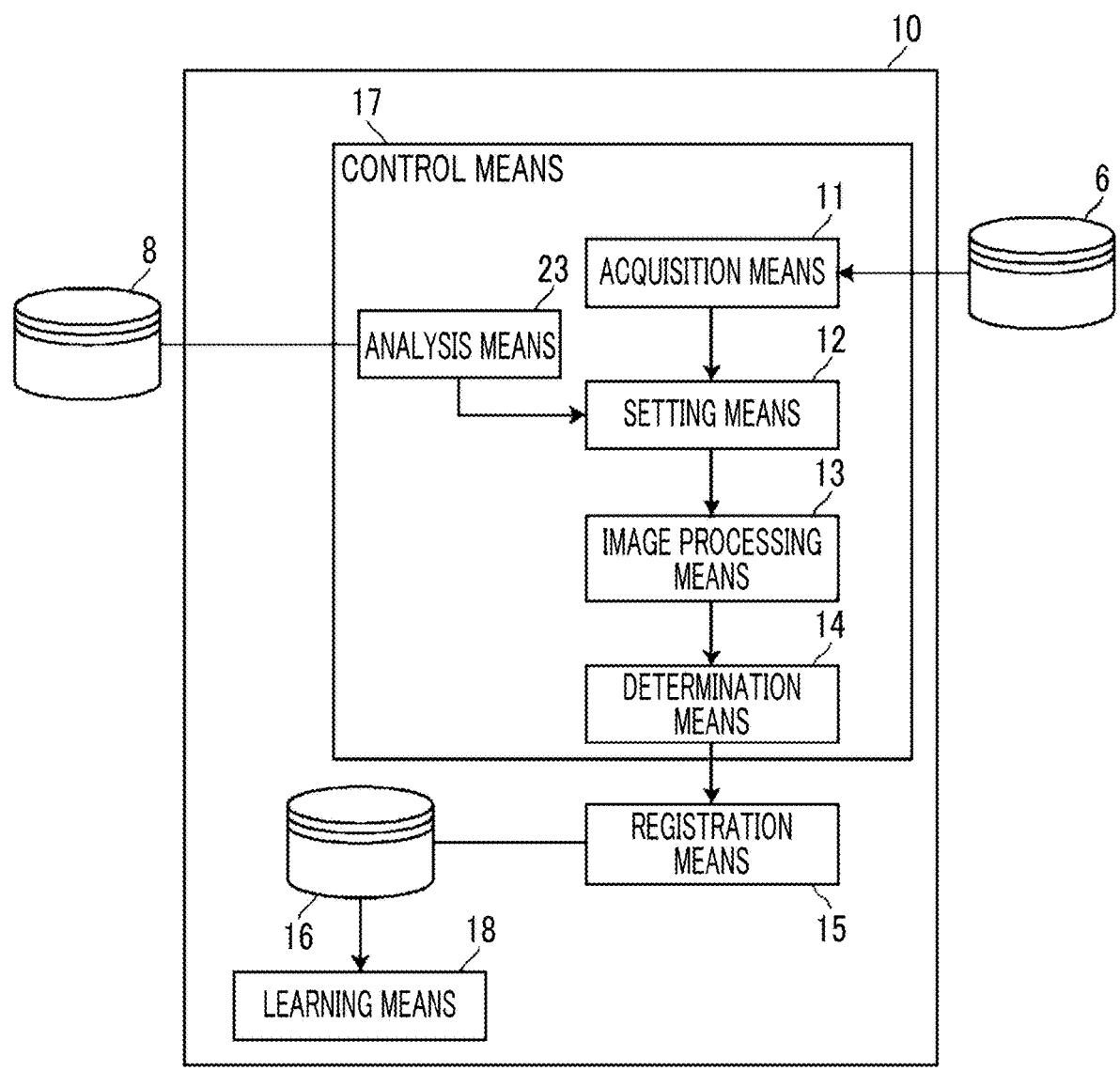
FIG. 2 is a diagram showing a schematic configuration of a learning data generation support apparatus according to a first embodiment of the invention.
Figure 3:
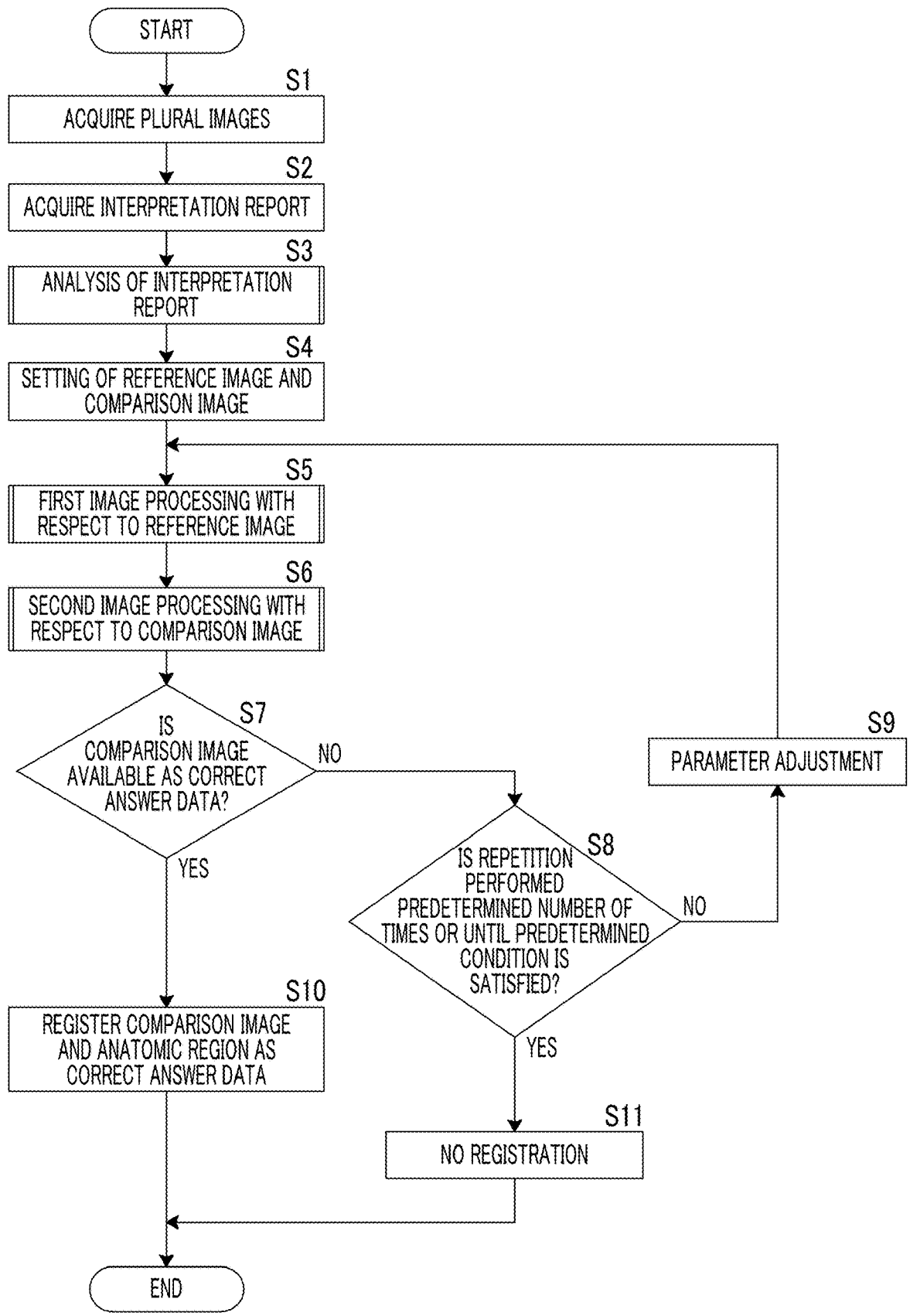
FIG. 3 is a flowchart showing a flow of a process of registering correct answer data.

Next, the learning data generation support apparatus 10 according to the first embodiment of the invention will be described in detail with reference to FIGS. 1 to 3. FIG. 2 is a functional block diagram showing a configuration of the learning data generation support apparatus 10, and FIG. 3 is a flowchart showing a flow of a process of the learning data generation support apparatus 10.

The learning data generation support apparatus 10 of the invention is connected to the network 9, and is connected to the image database 6 and the interpretation report database 8 through the network 9 (see FIG. 1).

The learning data generation support apparatus 10 is configured of a general-purpose computer, and includes a known hardware configuration such as a CPU, a main storage, an auxiliary storage, an input/output interface, a communication interface, an input device, a display device, a data bus, and the like. In learning data generation support apparatus 10, a known operation system, an application program, or the like is installed, and a learning data generation support program of the invention is also installed. Further, the learning data generation support apparatus 10 performs transmission and reception of data with respect to the image database 6 and the interpretation report database 8 connected to the network 9 through a communication interface. The learning data generation support program may be installed from a recording medium such as a compact disc read only memory (CD-ROM), or may be installed through a network such as the Internet.

As shown in FIG. 2, the learning data generation support apparatus 10 includes acquisition means 11, setting means 12, image processing means 13, determination means 14, registration means 15, control means 17, and learning means 18.

The acquisition means 11 acquires two or more different inspection images (hereinafter, simply referred to as images) obtained by imaging the same portion of a subject (patient). The acquisition means 11 transmits a patient ID for specifying the patient and portion information to the image management server 5 to request images obtained by imaging the same portion among images to which the same patient ID is allocated. The image management server 5 retrieves and receives the images obtained by imaging the same portion among the images obtained by imaging the same patient from the image database 6 using the DICOM tag. The received images are once stored in an auxiliary storage device such as a hard disk of the learning data generation support apparatus 10. The different images may be images captured using different kinds of modalities 2, images captured through different imaging protocols using the same kind of modality 2, images captured at different time points using the same modality 2, or the like. The images captured through the different imaging protocols using the same kind of modality 2 may be a T1 weighted image and a T2 weighted image captured using a T1 imaging protocol and a T2 imaging protocol of an MRI apparatus, for example.

The setting means 12 sets any one of a plurality of acquired images as a reference image on the basis of an imaged portion or disease information, and sets images other than the reference image as comparison images. The image set as the reference image is determined on the basis of the kind of each image, an imaging time point of each image, or a combination of the kind of each image and the imaging time point of each image, according to an imaged portion in the plurality of images. Alternatively, the image set as the reference image is determined on the basis of the kind of each image, an imaged portion, an imaging time point of each image, or a combination thereof, according to a disease.

Information on the imaged portion may be acquired on the basis of information recorded in a DICOM tag. Information on the disease may be obtained from an interpretation report stored in association with each of the acquired images. The interpretation report is requested of the interpretation report server 7, and the requested interpretation report is retrieved from the interpretation report database 8 for reception. The received interpretation report is once stored in an auxiliary storage device such as a hard disk of the learning data generation support apparatus 10. Further, the interpretation report is analyzed to acquire disease information (details of the analysis of the interpretation report will be described later). In addition, with respect to the information on the portion, similarly, by analyzing the interpretation report, it is possible to acquire detailed information compared with the information on the portion stored in the DICOM tag, and thus, it is possible to use the information in a case where the reference image is set.

According to a detection target such as an organ or a lesion, there is a case where the kind of an image for which the most accurate result is obtained in a case where an organ extraction process or a lesion detection process is executed is determined. In a case where there are two or more kinds of images, even in a case where the same organ extraction process is performed, the kind of image for which a more accurate result is expected to be obtained is set as a reference image. Further, there is a case where the kinds of images for which the most accurate result is obtained are determined in such a manner that a result detected from a CT image is correct with respect to a lesion of a specific disease but a result detected from an MRI image is correct with respect to a lesion of a different disease. Among a plurality of images, the kind of an image for which a more accurate result is obtained in accordance with image processing is set as a reference image, and different images are set as comparison images.

Further, in a case where the organ extraction process and the lesion detection process are performed, the organ extraction process does not obtain a very inaccurate result, but the lesion detection process may not obtain an accurate result due to the influence of overlapping of another tissue such as a bone or another organ. Accordingly, an image to be used in the organ extraction process may be set as a reference image, and an image to be used in the lesion detection process may be set as a comparison image.

Further, in a case where the progress of the same portion is observed, among a current image and a past image (that represents an image captured before the current image is captured), for example, the past image may be set as a reference image, and the current image may be set as a comparison image.

The above-described determination of the reference image may be performed according to a predetermined rule. For example, a file in which a rule is written or a table in which relationships between reference images and comparison images are shown is stored in advance in an auxiliary storage device of the learning data generation support apparatus 10, and the setting means 12 sets a reference image and a comparison image with reference to the above-mentioned file or table. Further, relationships between reference images and comparison images may be provided in a learning data generation support program. Alternatively, a doctor may designate an image that is a reference image, and may set a different image as a comparison image.

The analysis means 23 analyzes a character string in an interpretation report associated with each acquired image, and extracts information relating to a disease recorded in the interpretation report or information relating to a portion recorded in the interpretation report. Specifically, by performing natural language processing, dividing a sentence in the interpretation report into words, and analyzing the order of the words, the analysis means 23 acquires information relating to the disease or the portion. As necessary, terms such as a disease name, a lesion name, and a portion name are registered in advance, and contents written in the report are extracted from character strings that match the terms.

The disease information may be obtained from the disease name, but may be estimated from information from which a disease name such as a lesion name, for example, a pulmonary nodule can be estimated. The terms may be prepared in advance through a medical term dictionary, and a plurality of terms that represent the same disease or the same portion may be registered in a dictionary. Then, in a case where a term recorded in an interpretation report represents the same disease or the same portion, the terms may be considered as the same terms. In addition, as in an obscure search, even in a case where a term does not completely match a term in a dictionary under a certain rule, it may be determined whether the terms match each other using a term that is most similar to the term in the dictionary.

The image processing means 13 executes a first image processing of extracting an anatomic region with respect to a reference image and executes a second image processing of extracting an anatomic region with respect to a comparison image, according to a portion or a disease. As the kinds of image processings of extracting the anatomic regions, an organ extraction process, a lesion detection process, and the like may be used. The first image processing and the second image processing may be the same kinds of processings, or one may be the organ extraction process and the other may be the lesion detection process. Alternatively, one of the first image processing and the second image processing may be a combination process of the organ extraction process and the lesion detection process, or both of the first image processing and the second image processing may be a combination process of the organ extraction process and the lesion detection process. The organ extraction process and the lesion detection process may use a graph cut. For example, a graph cut technique disclosed in Japanese Patent No. 4493679 may be used.

The organ extraction process may include a region division process of dividing an extracted organ into a plurality of regions. For example, the brain may be divided into sections, or the heart may be divided into the right and left ventricles and atriums.

In a case where a reference image and a comparison image are determined according to a portion, the first image processing to be performed with respect to the reference image and the second image processing to be performed with respect to the comparison image may be determined in accordance with a portion, the kind of the reference image, the kind of the comparison image, or a combination thereof. Alternatively, in a case where a reference image and a comparison image are determined according to a disease, the first image processing to be performed with respect to the reference image and the second image processing to be performed with respect to the comparison image may be determined in accordance with a disease, a portion, the kind of the reference image, the kind of the comparison image, or a combination thereof.

The determination means 14 determines whether a comparison image is available as correct answer data using an image processing result of a reference image in the first image processing and an image processing result of the comparison image in the second image processing. Particularly, the determination may be performed using anatomic regions obtained by extracting the anatomic regions using the image processings, in which the determination may be performed by comparing the sizes of the anatomic regions or comparing ranges of the anatomic regions. As the anatomic regions that are determination targets, an organ region obtained by the organ extraction process and a lesion region obtained by the lesion detection process may be used. For example, in the organ extraction process, there is a case where an accurate result is obtained in a case where the anatomic regions are extracted from a CT image compared with a case where the anatomic regions are extracted from an MRI image. Further, in the lesion detection process, according to lesions, there is a case where a clear lesion can be detected in the case of an MRI image compared with the case of a CT image, but contrarily, there is a case where a clear lesion can be detected in the case of the CT image compared with the case of the MRI image. In addition, in a past image and a current image, there are few cases where the size of an organ extracted in an organ extraction process greatly changes. Alternatively, in the case of a lesion that is present in a specific organ, a result of a lesion detection process should be detected in a range of an organ obtained as a result of a specific organ extraction process. On the basis of the knowledge obtained from such an experience, an anatomic region obtained from a reference image is compared with an anatomic region obtained from a comparison image from combinations of various kinds of images and various kinds of image processings (the kind of the first image processing and the kind of the second image processing), a criterion for determining whether the comparison image is available as correct answer data is set in advance, and it is determined whether the comparison image is available as the correct answer data. Alternatively, it is determined whether the anatomic region obtained from the comparison image in addition to the comparison image is available as the correct answer data.

Hereinafter, a specific example will be described. For example, a case where three images of a specific patient are acquired from an image database will be described. In a case where these imaging portions are the abdomen, and in a case where an image 1 is a CT image (past image), an image 2 is a CT image (current image), and an image 3 is an MRI image, the image 1 that is the past image is selected as a reference image, and the image 2 that is the current image is selected as a comparison image. In a case where there is no big difference between the sizes of extracted livers in a result obtained by performing a liver extraction process (first image processing) with respect to the image 1 and a result obtained by performing a liver extraction process (second image processing) with respect to the image 2, it is determined that the image 2 is an image that is available as correct answer data. In a case where there is a difference equal to or greater than a predetermined reference, for example, a difference of 1.2 or more times in volume, it is determined that the image 2 is not available as the correct answer data.

With respect to the organ extraction process, in a case where an extraction result is acquired from a CT image, an approximately accurate result is obtained. On the other hand, it is possible to perform the organ extraction process even in an MRI image, but there is a case where an extraction result is not correct. For example, in the case of the liver, it is not possible to accurately detect a contour of the liver in the MRI image, and there is a case where its size is detected to be larger than the size of an actual liver. Thus, the image 1 that is the CT image is set as a reference image, and the image 3 that is the MRI image is set as a comparison image. In a case where there is no big difference between the sizes of extracted livers in a result obtained by performing a liver extraction process for a CT image with respect to the image 1 and a result obtained by performing a liver extraction process for an MRI image with respect to the image 3, it is determined that the image 3 is an image that is available as correct answer data. In a case where there is a difference equal to or greater than a predetermined reference, for example, it is determined that the image 3 is not available as the correct answer data.

Detection of a lesion of a lung disease is mainly performed using an X-ray chest image or a CT chest image. A case where two X-ray chest images of a patient having a lung disease are acquired from an image database will be described. It is assumed that imaging portions in these images correspond to the chest, and it is assumed that an image 1 is an X-ray chest image (past image) and an image 2 is an X-ray chest image (current image). The image 1 is set as a reference image, and the image 2 is set as a comparison image. A lung field extraction process (first image processing) is performed with respect to the image 1, and a pulmonary nodule detection process (second image processing) is performed with respect to the image 2. According to whether or not a region of the pulmonary nodule detected from the image 2 is present within the lung field region extracted from the image 1, it is possible to determine whether the comparison image is available as correct answer data. Here, in a case where a registration process is performed between the image 1 and the image 2 before the image processings are performed, it is possible to accurately determine whether the pulmonary nodule is present within the lung field region extracted from the image 1.

An MRI image is generally used in diagnosis of the brain such as cerebral infarction. In MRI imaging, T1 weighting, T2 weighting, diffusion weighted imaging (DWI), and the like are known as imaging protocols. Generally, in an MR image of the brain, a T1 weighted image and a T2 weighted image are useful for recognizing an anatomic structure, and the DWI is useful for detecting cerebral infraction. A case where two images of a patient having cerebral infraction are acquired from an image database will be described. It is assumed that imaging portions in these images correspond to the head, and it is assumed that an image 1 is a T1 weighted image and an image 2 is a DWI image. The image 1 is set as a reference image, and the image 2 is set as a comparison image. A region division process (first image processing) is performed with respect to the image 1, and a lesion detection process (second image processing) is performed with respect to the image 2. Further, it is possible to determine whether the image 2 is available as correct answer data from a generation position of cerebral infraction extracted from an interpretation report.

In a case where the determination means 14 determines that the comparison image is available as the correct answer data, the registration means 15 registers the comparison image in a registration part 16 as the correct answer data. The registration part 16 is configured of a large capacity storage that stores images. Alternatively, the registration part 16 may register only IDs of images, and the images may be read out from the image database 6 in learning. Further, the registration means may register an anatomic region obtained as a result obtained by performing the second image processing with respect to the comparison image, together with the comparison image, in addition to the comparison image.

The control means 17 controls processing flows of the acquisition means 11, the setting means 12, the image processing means 13, the determination means 14, and the registration means 15. In a case where it is determined by the determination means 14 whether a comparison image is available as correct answer data, the procedure proceeds to the registration means 15, but in a case where it is determined by the determination means 14 whether the comparison image is not available as the correct answer data, the procedure returns to the image processing means 13 again to execute the first image processing and the second image processing while adjusting a parameter. For example, an image analysis process is executed again after a calculation method of t-link or n-link in a graph cut is adjusted, as disclosed in Japanese Patent No. 4493679. A difference in density or light and shade appears in an image due to a difference between imaging conditions or modalities, but it is possible to find a correct result by repeatedly executing an image analysis process while adjusting a parameter as described above.

Further, in a case where it is determined that a comparison image is not available as correct answer data even the control means 17 adjusts the parameter to repeat the first image processing and the second image processing a predetermined number of times or until a predetermined condition is satisfied, the procedure is terminated without proceeding to the registration means 15. Alternatively, in a case where a comparison image is not available as correct answer data even though the parameter is adjusted a predetermined number of times until a predetermined condition is satisfied to repeat the first and second image processings, the procedure may be terminated without proceeding to the registration means 15. Whether or not the predetermined condition is satisfied may be determined according to whether the adjustment is performed within a range where a parameter value is changeable, or may be determined according to whether the adjustment is performed within a range determined according to a predetermined rule such as a combination of one parameter value and another parameter value. Specifically, in order to adjust a parameter, a parameter value may be repeatedly changed at a predetermined interval to perform the first and second image processings.

Hereinafter, a registration method of correct answer data will be described in detail using a flowchart of FIG. 3 with reference to an example of a lung disease.

First, images of a patient are extracted from the image database 6 by the acquisition means 11 (S1). A plurality of X-ray chest images captured at different dates and times are acquired from the image database, and are once stored in a hard disk.

Then, the setting means 12 acquires an interpretation report associated with each X-ray chest image of the patient from the interpretation report database 8 (S2). By executing natural language processing with respect to the interpretation report using the analysis means 23, character strings corresponding to "disease name" and "lesion name" are extracted, respectively (S3). In a case where "there is a limbic-spine-form pulmonary nodule of 2.5 cm in a right upper lobe" is recorded in the interpretation report, "pulmonary nodule" is extracted as a character string corresponding to the "lesion name". Here, an X-ray chest image captured at the oldest imaging time point is set as a reference image, and an X-ray chest image captured at the latest imaging time point is set as a comparison image (S4).

Then, the image processing means 13 performs a lung field extraction process (first image processing) with respect to the reference image (S5), and performs a pulmonary nodule detection process (second image processing) with respect to the comparison image (S6). The determination means 14 determines whether a region of the pulmonary nodule detected from the comparison image is present within a lung field region extracted from the reference image (S7). In a case where the region of the pulmonary nodule is present within the lung field region, the determination means 14 determines that the comparison image is available as correct answer data (YES in S7). The control means 17 causes the procedure to proceed to S10, and then, the registration means 15 registers the comparison image and the region of the pulmonary nodule extracted from the comparison image in the registration part 16 as the correct answer data (S10).

On the other hand, in a case where the comparison image is not available as the correct answer data (NO in S7 and NO in S8), the control means 17 adjusts a parameter of the image processings (S9), and then, causes the procedure to proceed to the first image processing and the second image processing again (S5 and S6). The adjustment of the parameter is performed according to a predetermined rule. Thus, the parameter is changed, and the image processings are repeated (S5 to S9). In a case where the comparison image is not available as the correct answer data even though the image processings are repeated (NO in S7 and YES in S8), the correct answer data is not registered (S11). The repetition is performed a predetermined number of times. Alternatively, the repetition may be performed until a predetermined condition is satisfied (S8).

The learning means 18 performs machine learning based on a neural network using the correct answer data registered in the registration part 16 as the correct answer data by the registration means 15. Specifically, for example, by using a convolutional neural network, or the like, an image recognition device may be generated.

Then, a second embodiment will be described. In this embodiment, in a case where a determination means determines that a comparison image is not available as correct answer data, a case where an image processing result of the comparison image is modified to be registered as correct answer data will be described. In this embodiment, a learning data generation support apparatus 10a of this embodiment is provided in the medical information system 1 in a similar way to the first embodiment, and the learning data generation support apparatus 10a is connected to the network 9, and is connected to the image database 6 and the interpretation report database 8 through a network.

Figure 4:
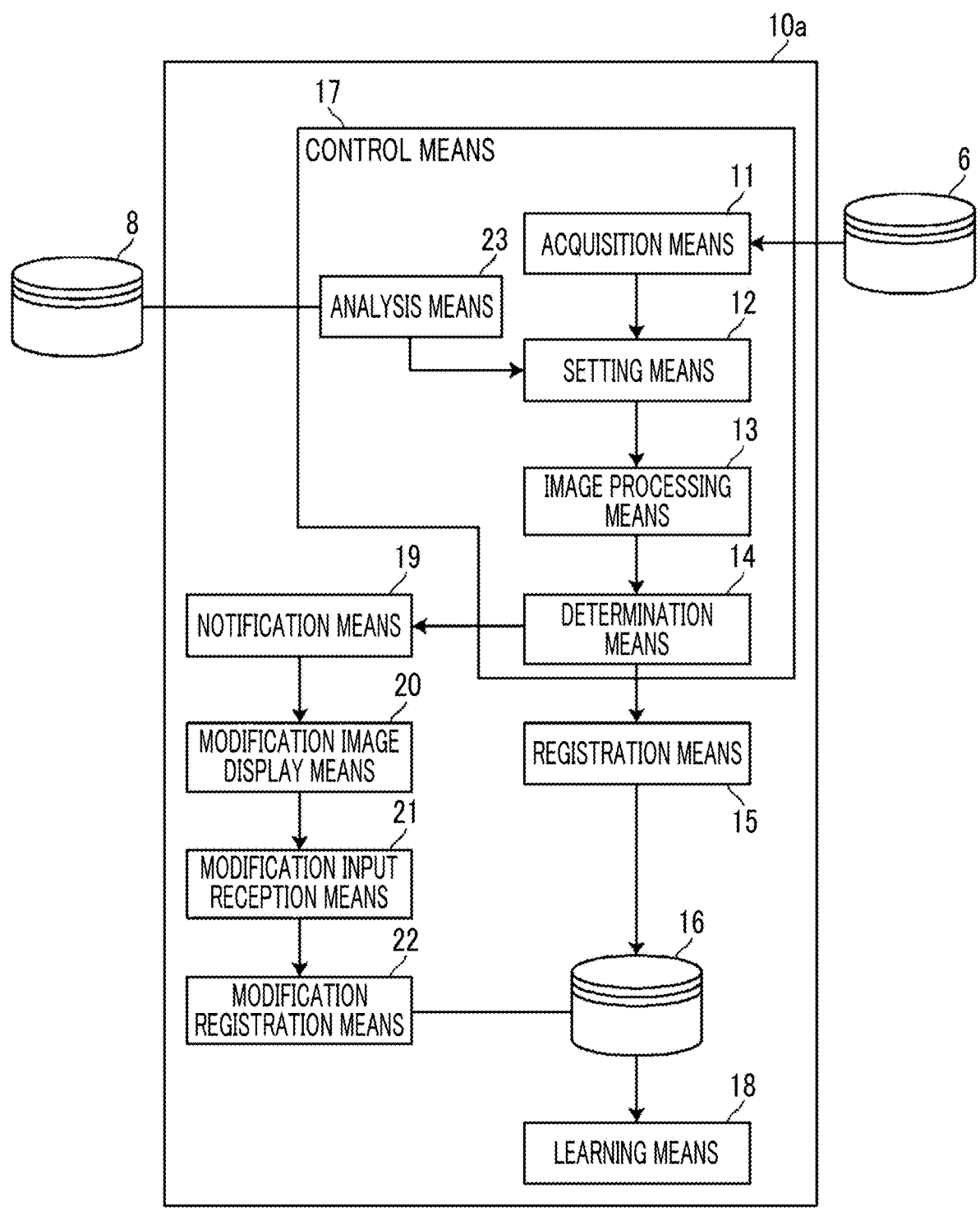
FIG. 4 is a diagram showing a schematic configuration of a learning data generation support apparatus according to a second embodiment of the invention.
Figure 5:
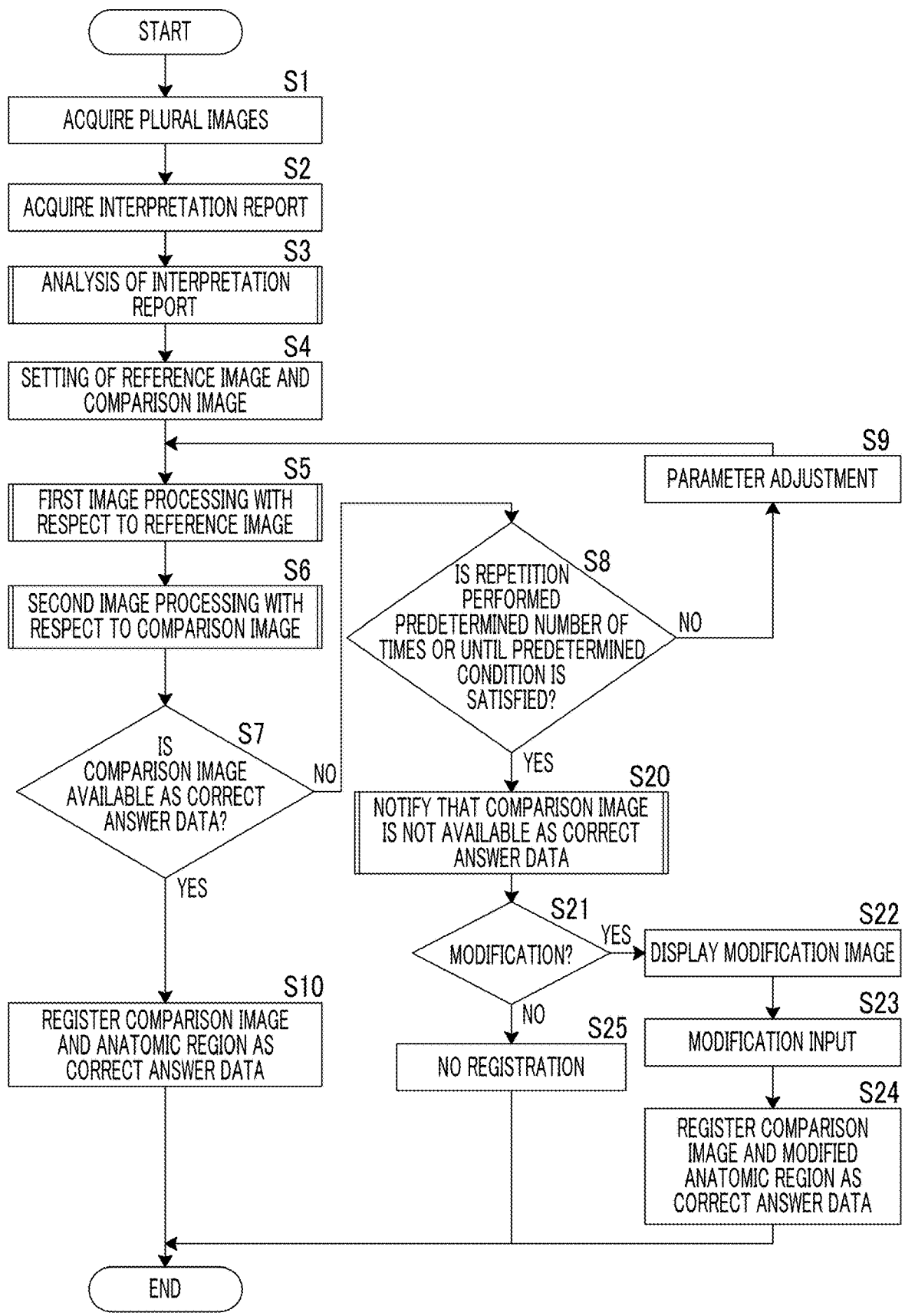
FIG. 5 is a flowchart showing a flow of a process of modifying an image processing result obtained from a comparison image.
Figure 6:
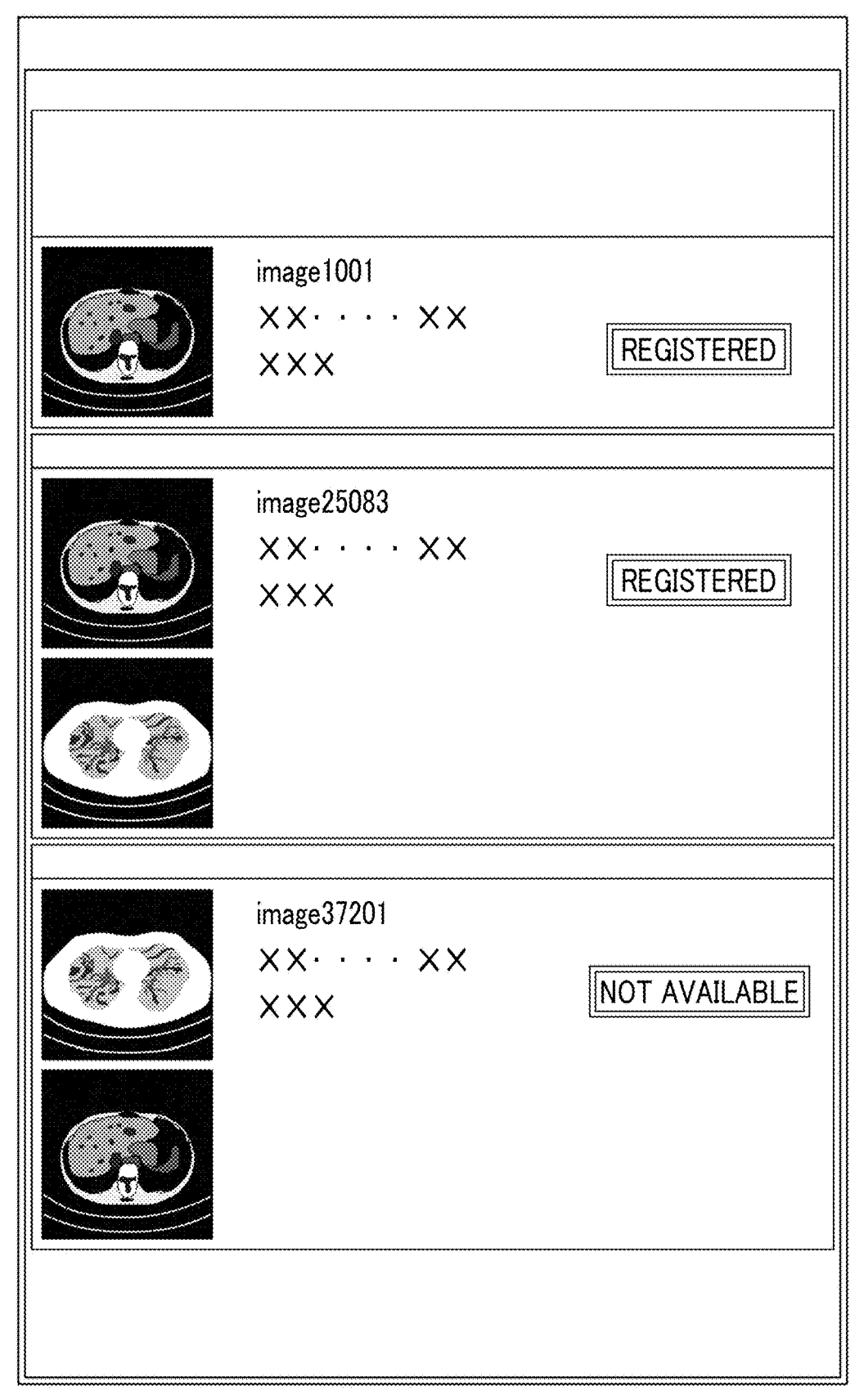

Hereinafter, the learning data generation support apparatus of the second embodiment will be described with reference to FIGS. 4 to 6. FIG. 4 is a functional block diagram showing a configuration of the learning data generation support apparatus 10a according to the second embodiment. The same reference numerals are given to the same configurations as in the learning data generation support apparatus 10 of the first embodiment, and detailed description thereof will not be repeated. FIG. 5 is a flowchart showing a processing flow of the learning data generation support apparatus 10a. FIG. 6 is a display example of a display screen.

As shown in FIG. 4, the learning data generation support apparatus 10a includes the acquisition means 11, the setting means 12, the image processing means 13, the determination means 14, the registration means 15, the control means 17, notification means 19, modification image display means 20, modification input reception means 21, modification registration means 22, and the learning means 18.

In a case where the determination means 14 determines that a comparison image is not available as correct answer data, the notification means 19 notifies that the comparison image is not available. For example, as shown in FIG. 6, a list of thumbnail images of comparison images for which determination is performed and images that represent anatomic regions extracted from the comparison images is displayed, a display of "registered" is performed on a comparison image determined to be available and registered as correct answer data, and a display of "unavailable" for notifying that it is necessary to modify an extracted anatomic region is performed on a comparison image determined to be unavailable. In FIG. 6, displays using characters are performed, but in order to recognize whether registration is finished and whether a comparison image is not available and an extracted anatomic region needs to be modified, colors of frames that show results in the list may be changed. As necessary, determination results or information recorded in a DICOM tag, such as an image ID, may be displayed.

Alternatively, the notification means 19 may retrieve only an image determined to be unavailable by the determination means 14 to perform a list display. Further, the notification means 19 may display purposes for which correct answer data is prepared, and thus, may make it possible to confirm which image is registered and which image needs to be modified, for each purpose.

The modification image display means 20 displays, with respect to a comparison image notified to be unavailable, an anatomic region such as a lesion region or an organ region obtained from the comparison image in a recognizable manner. Specifically, for example, as a modification screen, an image obtained by image fusion of a reference image and a comparison image that is a modification target may be displayed. Alternatively, an anatomic region obtained from the comparison image may be displayed to be surrounded by a line of a specific color such as a red color, and an anatomic region extracted from the reference image may be displayed to be surrounded by a line of another color such as a green color.

The modification input reception means 21 receives an input for modifying an anatomic region obtained as an image processing result of a comparison image. Further, the modified anatomic region is stored as a modification result. For example, modification, deletion or addition of a contour of an anatomic region obtained from a comparison image may be performed on a mixed image using a pointing device such as a mouse, and its result may be stored as the anatomic region. For example, in a case where liver extraction is performed using a CT image as a reference image and using an MRI image as a comparison image, the modification input reception means 21 displays the CT image obtained by imaging the liver as the reference image, receives an input for modifying a contour of a liver region extracted from the MRI image to be close to a liver region extracted from the CT image, and stores the modified liver region. Alternatively, in a case where a lung field region is extracted from a past image using the past image obtained by imaging the chest as a reference image and a pulmonary nodule is extracted from a current image using the current image as a comparison image, the modification input reception means 21 deletes a part of a region of the pulmonary nodule obtained from the comparison image outside a lung field region obtained from the reference image. A region of the pulmonary nodule after the part is deleted is stored.

The modification registration means 22 registers the anatomic region of the comparison image modified as described above and the comparison image in the registration part 16 as correct answer data.

Hereinafter, with reference to an example of extraction of a liver region, a method for modifying an anatomic region obtained as an image processing result of a comparison image after it is determined by the determination means 14 that the comparison image is not available as correct answer data will be described in detail with reference to a flowchart of FIG. 5. Since processes of S1 to S10 are the same as in FIG. 2, detailed description of will not be repeated.

In a case where a comparison image is not available as correct answer data even though image processings are repeated while changing a parameter (NO in S7 and YES in S8), the notification means 19 notifies that the comparison image is not available using a list display so that the comparison image determined to be unavailable can be confirmed, as shown in FIG. 6 (S20).

A user selects an image in which a liver region is extracted as a comparison image to be modified from comparison images determined to be unavailable. In a case where the comparison image is selected as a modification target (YES in S21), the modification image display means 20 mixes an MRI image that is the comparison image and a CT image that is a reference image by image fusion, and displays an image in which a contour of a liver region extracted from the MRI image is displayed on the mixed image as a modification image (S22). The modification input reception means 21 receives a modification input for modifying the contour of the liver region using a mouse or the like from the user, and modifies and stores the contour of the liver region (S23). The modification registration means 22 registers an anatomic region of the modified comparison image and the comparison image as correct answer data (S24).

Further, in a similar way to the first embodiment, the learning means 18 performs machine learning based on a neural network using correct answer data registered in the registration part 16 as correct answer data by the modification registration means 22, in addition to correct answer data registered by the registration means 15.

As specifically described above, it is possible to acquire a large amount of various correct answer data necessary for machine learning using images stored in a medical image management system.

What is claimed is:

1. A learning data generation support apparatus comprising:
   processing circuitry configured to:
   acquire two or more different images obtained by imaging the same portion of a subject;
   set any one of the acquired images as a reference image and set an image other than the reference image among the acquired images as a comparison image, according to the portion or a disease;
   execute a first image processing of extracting an anatomic region with respect to the reference image according to the portion or the disease, and execute a second image processing of extracting an anatomic region with respect to the comparison image according to the portion or the disease;
   determine whether the comparison image is available as correct answer data using a result of whether the anatomic region of the comparison image extracted by the second image processing has an appropriate position, size, and/or range for the anatomic region of the reference image extracted by the first image processing; and
   register the comparison image determined to be available as the correct answer data as the correct answer data;
   the processing circuitry further configured to:
   analyze a character string in an interpretation report of each of the two or more images, and
   determine the reference image and the comparison image according to the portion or the disease that is obtained.

2. The learning data generation support apparatus according to claim 1,
   wherein the processing circuitry is further configured to register the comparison image and the anatomic region obtained from the comparison image as the correct answer data.

3. The learning data generation support apparatus according to claim 1,
   wherein the first image processing and the second image processing correspond to at least one of an organ extraction process or a lesion detection process.

4. The learning data generation support apparatus according to claim 1,
   wherein the kind of the first image processing is different from the kind of the second image processing.

5. The learning data generation support apparatus according to claim 1,
   wherein the two or more different images are images captured using two or more different kinds of imaging apparatuses.

6. The learning data generation support apparatus according to claim 5,
   wherein the two or more different kinds of imaging apparatuses are two or more kinds of imaging apparatuses among an MRI apparatus, a CT apparatus, a CR apparatus, a PET apparatus, and an ultrasonic imaging apparatus.

7. The learning data generation support apparatus according to claim 1,
   wherein the two or more different images are images captured at different imaging protocols using the same kind of imaging apparatus.

8. The learning data generation support apparatus according to claim 7,
   wherein the same kind of imaging apparatus is an MRI apparatus, and the different imaging protocols are a T1 imaging protocol and a T2 imaging protocol.

9. The learning data generation support apparatus according to claim 1,
   wherein the two or more different images are images captured at different time points using the same kind of imaging apparatus.

10. A learning data generation support apparatus comprising:
    processing circuitry configured to:
    acquire two or more different images obtained by imaging the same portion of a subject;
    set any one of the acquired images as a reference image and set an image other than the reference image among the acquired images as a comparison image, according to the portion or a disease;
    execute a first image processing of extracting an anatomic region with respect to the reference image according to the portion or the disease, and execute a second image processing of extracting an anatomic region with respect to the comparison image according to the portion or the disease;
    determine whether the comparison image is available as correct answer data using a result of whether the anatomic region of the comparison image extracted by the second image processing has an appropriate position, size, and/or range for the anatomic region of the reference image extracted by the first image processing; and
    register the comparison image determined to be available as the correct answer data as the correct answer data, wherein the processing circuitry is further configured to:
register the comparison image and the anatomic region obtained from the comparison image as the correct answer data;
notify that the comparison image is not available in a case where it is determined that the comparison image is not available as the correct answer data;
wherein the processing circuitry is further configured to:
display the anatomic region of the comparison image for which it is notified that the comparison image is not available in a recognizable manner;
receive an input for modifying the anatomic region of the comparison image; and
register the anatomic region of the comparison image modified according to the input that is received and the comparison image as the correct answer data.

11. An operation method of a learning data generation support apparatus that includes processing circuitry, the operation method comprising:
acquiring two or more different images obtained by imaging the same portion of a subject;
setting any one of the acquired images as a reference image, and setting an image other than the reference image among the acquired images as a comparison image, according to the portion or a disease;
executing a first image processing of extracting an anatomic region with respect to the reference image according to the portion or the disease, and executing a second image processing of extracting an anatomic region with respect to the comparison image according to the portion or the disease;
determining whether the comparison image is available as correct answer data using a result of whether the anatomic region of the comparison image extracted by the second image processing has an appropriate position, size, and/or range for the anatomic region of the reference image extracted by the first image processing; and
registering the comparison image determined to be available as the correct answer data as the correct answer data;
the method further comprising:
analyzing a character string in an interpretation report of each of the two or more images; and
determining the reference image and the comparison image according to the portion or the disease that is obtained.

12. A non-transitory computer-readable recording medium storing therein a learning data generation support program for causing a computer to:
acquire two or more different images obtained by imaging the same portion of a subject;
set any one of the acquired images as a reference image and set an image other than the reference image among the acquired images as a comparison image, according to the portion or a disease;
execute a first image processing of extracting an anatomic region with respect to the reference image according to the portion or the disease, and execute a second image processing of extracting an anatomic region with respect to the comparison image according to the portion or the disease;
determine whether the comparison image is available as correct answer data using a result of whether the anatomic region of the comparison image extracted by the second image processing has an appropriate position, size, and/or range for the anatomic region of the reference image extracted by the first image processing; and
register the comparison image determined to be available as the correct answer data as the correct answer data;
the program further causing the computer to:
analyze a character string in an interpretation report of each of the two or more images; and
determine the reference image and the comparison image according to the portion or the disease that is obtained.

* * * * *